US008562963B2

(12) United States Patent
Samson et al.

(10) Patent No.: US 8,562,963 B2
(45) Date of Patent: *Oct. 22, 2013

(54) OPHTHALMIC COMPOSITIONS COMPRISING POVIDONE-IODINE

(75) Inventors: C. Michael Samson, New York, NY (US); Bo Liang, East Brunswick, NJ (US); Joseph A. Capriotti, Los Mojones (ES)

(73) Assignee: CLS Pharmaceuticals, Inc., New York, NY (US)

( * ) Notice: Subject to any disclaimer, the term of this patent is extended or adjusted under 35 U.S.C. 154(b) by 3 days.

This patent is subject to a terminal disclaimer.

(21) Appl. No.: 12/814,836

(22) Filed: Jun. 14, 2010

(65) Prior Publication Data
US 2010/0254934 A1 Oct. 7, 2010

Related U.S. Application Data

(63) Continuation of application No. 11/636,293, filed on Dec. 7, 2006, now Pat. No. 7,767,217.

(60) Provisional application No. 60/782,629, filed on Mar. 14, 2006, provisional application No. 60/848,315, filed on Sep. 29, 2006.

(51) Int. Cl.
*A61K 31/74* (2006.01)

(52) U.S. Cl.
USPC .................................................. 424/78.04

(58) Field of Classification Search
USPC .................................................. 424/78.04
See application file for complete search history.

(56) References Cited

U.S. PATENT DOCUMENTS

| 3,886,268 | A |   | 5/1975  | Halpern |
|-----------|---|---|---------|---------|
| 4,001,388 | A |   | 1/1977  | Shell |
| 4,115,544 | A |   | 9/1978  | Shell |
| 4,177,268 | A |   | 12/1979 | Torossian et al. |
| 4,186,184 | A |   | 1/1980  | Zaffaroni |
| 4,865,846 | A |   | 9/1989  | Kaufman |
| 4,882,150 | A |   | 11/1989 | Kaufman |
| 4,976,969 | A | * | 12/1990 | Plamondon ............ 424/78.04 |
| 5,126,127 | A |   | 6/1992  | Bhagwat et al. |
| 5,149,693 | A |   | 9/1992  | Cagle et al. |
| 5,149,694 | A | * | 9/1992  | Cagle et al. .............. 514/40 |
| 5,178,853 | A | * | 1/1993  | Jauw ..................... 424/78.04 |
| 5,232,692 | A |   | 8/1993  | Isenberg et al. |
| 5,733,572 | A |   | 3/1998  | Unger et al. |
| 5,879,717 | A |   | 3/1999  | McConn-Stern et al. |
| 7,175,850 | B2 |  | 2/2007  | Cevc |
| 7,767,217 | B2 | * | 8/2010 | Samson et al. ............ 424/405 |
| 2002/0064524 | A1 | | 5/2002 | Cevc |
| 2003/0072732 | A1 | | 4/2003 | Breton et al. |
| 2005/0191270 | A1 | | 9/2005 | Gruening et al. |
| 2006/0002963 | A1 | | 1/2006 | Rabinovich-Guilatt et al. |
| 2006/0067978 | A1 | | 3/2006 | Heiler et al. |
| 2006/0068012 | A1 | | 3/2006 | Heiler et al. |
| 2006/0280809 | A1 | | 12/2006 | Leshchiner |

FOREIGN PATENT DOCUMENTS

| JP | 0363228      | 3/1991  |
| WO | 89/09057     | 10/1989 |
| WO | 00/72822     | 12/2000 |
| WO | 2005/056066  | 6/2005  |
| WO | 2007/106381  | 9/2007  |

OTHER PUBLICATIONS

Woodward, cis-Hydroxylation of a Synthetic Steroid Intermediate with Iodine, Silver Acetate, and Wet Acetic Acid, 80 J Am. Chem. Soc. 209-211 (1958).*
Woodward et al., "cis-Hydroxylation of a Synthetic Steroid Intermediate with Iodine, Silver Acetate and Wet Acetic Acid"; J. Am. Chem. Soc., 80(1): 209-211 (1958).
Hale, L.M., "The Treatment of Corneal Ulcer with Povidone-Iodine (Betadine)"; North Carolina Medical Journal; 30:54-56 (1969).
Roswell Pfister and Neal Burstein, The Effects of Ophthalmic Drugs, Vehicles, and Preservatives on Corneal Epithelium: A Scanning Electron Microscope Study, 15 Invest. Ophthalmol. Vis. Sci. 246 (Apr. 1976).
Berkelman et al., "Increased Bactericidal Activity of Dilute Preparations od Povidone-Iodine Solutions"; Journal of Clinical Microbiology, 15:635-639 (1982).
Gottardi, W. "The Influence of Chemical Behaviour of Iodine on the Germicidal Action of Disinfectant Solutions Containing Iodine"; Journal of Hospital Infection, 6:1-11 (1985).
Rackur, H., "New Aspects of Mechanism of Action of Povidone-Iodine"; Journal of Hospital Infection, 6:13-23 (1985).
Schuhman et al., "Clinical Experience with Povidone-Iodine Eye Drops in Patients with Conjunctivitis and Keratoconjunctivitis"; Journal of Hospital Infection, 6:173-175 (1985).
Gatti et al., "In Vitro Effectiveness of Povidone-Iodine on Acanthamoeba Isolates from Human Cornea"; Antimicrobial Agents Chemotherapy, 42:2232-2234 (1998).
Isenberg et al., "A Controlled Trial of Povidone-Iodine to Treat Infectious Conjunctivitis in Children"; American Journal of Ophthalmology, 134: 681-688 (2002).
Isenberg et al., "The Ocular Application of Povidone-Iodine"; Community Eye Health, 46:30-31 (2003).
Santos et al., "Toxicity corneum-conjuntival of eye drops of iodine-povidona: study experimental"; Arq. Bras. Quest. Oftalmol, 66:279-288 (2003).

* cited by examiner

*Primary Examiner* — Sean Basquill
(74) *Attorney, Agent, or Firm* — Morgan, Lewis & Bockius LLP

(57) ABSTRACT

A topical ophthalmic composition comprised of povidone-iodine 0.01% to 10.0% combined with a steroid or non-steroidal anti-inflammatory drug. This solution is useful in the treatment of active infections of at least one tissue of the eye (e.g., conjunctiva and cornea) from bacterial, mycobacterial, viral, fungal, or amoebic causes, as well as treatment to prevent such infections in appropriate clinical settings (e.g. corneal abrasion, postoperative prophylaxis, post-LASIK/LASEK prophylaxis). Additionally the solution is effective in the prevention of infection and inflammation in the post-operative ophthalmic patient.

2 Claims, No Drawings

OPHTHALMIC COMPOSITIONS COMPRISING POVIDONE-IODINE

RELATED APPLICATION

The present application is a continuation of copending U.S. application Ser. No. 11/636,293, filed 7 Dec. 2006, which claims Priority from U.S. Provisional Application Ser. No. 60/782,629, filed 14 Mar. 2006 and U.S. Provisional Application Ser. No. 60/848,315 filed 29 Sep. 2006, all of which are hereby incorporated by reference in their entireties.

BACKGROUND OF THE INVENTION

Infectious conjunctivitis is an ophthalmic disorder characterized by inflammation of the conjunctiva secondary to invasion of a microbe. Microbes capable of causing conjunctivitis in humans include bacteria (including *Mycobacteria* sp), viruses, fungi, or amoebae. Current treatment for bacterial conjunctivitis consists of antibiotic drops. Because antibiotic drops are ineffective against viral conjunctivitis, treatment of such infections consists only of relieving symptoms. Treatments for fungi and amoeba conjunctivitis consist of a small selection of medications which lacks anti-bacterial or anti-viral activity and which, in addition, is toxic to the ocular surface.

Diagnosis of the various causative agents such as bacteria, virus, or fungus, in infectious conjunctivitis is not economically feasible because accurate diagnosis requires sophisticated laboratory culture not easily integrated into the average healthcare practice. Because accurate diagnosis is impractical, most conjunctivitis is presumed to be bacterial without culturing and is treated with antibiotics. Antibiotic treatment is suboptimal because it is ineffective against viral or fungal conjunctivitis.

The use of steroids is approached cautiously in the setting of ocular infection. While steroids can have the benefit of reducing the severity of the inflammation in an acute infection, they are also known to increase susceptibility to certain infections.

Topical corticosteroids are routinely used to control ocular inflammation. Their mechanism of action involves the inhibition of the immune response and the subsequent tissue destruction that exuberant inflammation may cause. Corticosteroid has the undesirable side effect of limiting the body's intrinsic ability to fight infection. In fact, inopportune steroids usage can worsen the course of an infection secondary to mycobacteria, virus, or fungus. Thus, the use of a combined antimicrobial-steroid medication in ocular infections is recommended only under careful observation of a trained ophthalmologist because of these significant risks. In fact, Tobradex® (Alcon), the most commonly prescribed combination ophthalmic antimicrobial-steroid drug, specifically lists 'viral disease of the cornea and conjunctiva, mycobacteria infection, and fungal infection' as absolute contraindications to its use. Clearly, these combination drugs were not intended to be used in the face of infectious conjunctivitis in which bacterial infection cannot be confirmed.

In summary, there is currently no ophthalmic antimicrobial drug with broad activity against all the causes of conjunctivitis or keratitis, and there is currently no approved antimicrobial/steroid, or antimicrobial/non steroidal anti-inflammatory combination drug that can be safely used in infectious conjunctivitis or keratitis that can potentially be viral or fungal in origin.

SUMMARY OF THE INVENTION

The invention is an ophthalmic composition comprised of povidone-iodine 0.01%-10% (weight/weight or weight/volume) combined with an anti-inflammatory medication, a steroid, or a combination of both anti-inflammatory and a steroid. In a preferred embodiment, the povidone-iodine (PVP-I) is between 0.1% and 2.5%, between 0.5 and 2%, between 0.75 and 2%, between 0.8 and 2%, between 0.9 and 2%, between 1% and 2% or between 1% and 1.5%. In another embodiment, the total weight of the PVP-I, anti-inflammatory and steroid is between 0.1% and 4.5%. This solution is useful in the treatment of infections of the conjunctiva and cornea. The broad spectrum of povidone-iodine would allow this combination to be used in cases of ocular conjunctival or corneal infection caused by mycobacteria, viruses, fungi, and amoeba; this is in distinction to currently available combination antimicrobial-steroid ophthalmic compositions, which are contraindicated in the aforementioned infections. Additionally the solution will be useful in the infectious prophylaxis and inflammatory control of patients recovering from recent ophthalmic surgery. There are no currently available antimicrobial/anti-inflammatory or antimicrobial/steroid combinations useful for viral, fungal, mycobacterial and amoebic infections in the post-operative period.

One embodiment of the invention is directed to an ophthalmic composition suitable for topical administration to an eye, effective for treatment and/or prophylaxis of a microorganism infection or a disorder of at least one tissue of the eye. Prophylaxis may be, for example, prophylaxis from infection following surgery, prophylaxis from infection after birth for the newborn, or prophylaxis from accidental contact with contaminating material. Accidental contact with contaminating material may occur, for example, during surgery or during food processing. The composition comprises povidone-iodine in a concentration between 0.01% to 10%, and an anti-inflammatory, a steroid, or a combination thereof.

The mammalian eye can be divided into two main segments: the anterior segment and the posterior segment. The anterior segment is the front third of the eye that includes the tissues in front of the vitreous humor: the cornea, iris, ciliary body, and lens. Within the anterior segment are two fluid-filled spaces: the anterior chamber and the posterior chamber. The anterior chamber is located between the posterior surface of the cornea (i.e. the corneal endothelium) and the iris. The posterior chamber is located between the iris and the front face of the vitreous. The posterior segment is the back two-thirds of the eye that includes the anterior hyaloid membrane and all tissues behind it: the vitreous humor, retina, choroid, and optic nerve. In some animals, the retina contains a reflective layer (the tapetum lucidum) which increases the amount of light each photosensitive cell perceives, allowing the animal to see better under low light conditions.

It was surprising to discover that the formulations of povidone-iodine combined with steroids, when present in a suitable pH range, eliminated the undesired irritating effect of PVP-I to the eye. The invention provides pH stable aqueous suspensions of water-insoluble drugs that remain in such a state even after extended periods of storage.

In a preferred embodiment, the ophthalmic composition contains povidone-iodine at a concentration between 0.1% and 2.5% by weight, or more preferably, between 0.5% and 2% by weight. In another preferred embodiment, the ophthalmic composition has a total weight of povidone-iodine, an anti-inflammatory, a steroid of between 0.1% to 2.5% (weight to volume, or weight to weight) or between 0.1% to 4.5%.

The steroid of the ophthalmic composition may be at a concentration of between 0.01 and 10%. In a preferred embodiment, the steroid is at a concentration of between 0.05 and 2%.

The ophthalmic composition may further comprise (1) a topical anesthetic which relieves pain (2) a penetration enhancer which enhances the penetration of povidone-iodine into the tissues of the eye (this may be a topical anesthetic) (3) an antimicrobial preservative, which, for example, may be at a concentration of about 0.001% to 1.0% by weight; (4) a co-solvent or a nonionic surface agent—surfactant, which, for example, may be about 0.01% to 2% by weight; (5) viscosity increasing agent, which, for example, may be about 0.01% to 2% by weight; and (6) a suitable ophthalmic vehicle.

The ophthalmic composition may be in the form of a solution, a suspension, an emulsion, an ointment, a cream, a gel, or a controlled-release/sustain-release vehicle. For example, the composition may be in the form of a contact lens solution, eyewash, eyedrop, and the like.

The ophthalmic composition may be used for treatment and/or prophylaxis of a microorganism infection. The microorganism may be a bacterium, a virus, a fungus, or an amoeba, a parasite, or a combination thereof. The bacteria may be a mycobacterium. Further, the solution may be used to treat or for prophylaxis of disorders such as conjunctivitis, corneal abrasion, ulcerative infectious keratitis, epithelial keratitis, stromal keratitis and herpesvirus-related keratitis.

For example, the ophthalmic composition may comprise the following: 0.5 to 2% (w/w) polyvinylpyrrolidinone-iodine complex; 0.05 to 2% (w/w) steroid; 0.005% to 0.02% (w/w) EDTA (ethylenediaminetetraacetic acid); 0.01 to 0.5% (w/w) sodium chloride; 0.02 to 0.1% (w/w) tyloxapol; 0.5% to 2% (w/w) sodium sulfate; and 0.1 to 0.5% (w/w) hydroxyethylcellulose; at pH range from 5 to 7. More specifically, the ophthalmic composition may comprise the following: 1.0% (w/w) polyvinylpyrrolidinone-iodine complex; 0.1% (w/w) steroid; 0.01% (w/w) EDTA dehydrate; 0.3% (w/w) sodium chloride salt; 0.05% (w/w) tyloxapol; 1.2% (w/w) sodium sulfate; and 0.25% (w/w) hydroxyethylcellulose; at pH range from 5.5 to 6.5. In one embodiment, the composition consists essentially of 0.5 to 2% (w/w) polyvinylpyrrolidinone-iodine complex; 0.05 to 2% (w/w) steroid; 0.005% to 0.02% (w/w) EDTA (ethylenediaminetetraacetic acid); 0.01 to 0.5% (w/w) sodium chloride; 0.02 to 0.1% (w/w) tyloxapol; 0.5% to 2% (w/w) sodium sulfate; and 0.1 to 0.5% (w/w) hydroxyethylcellulose; at pH range from 5 to 7. In another embodiment, the composition consists essentially of 1.0% (w/w) polyvinylpyrrolidinone-iodine complex; 0.1% (w/w) steroid; 0.01% (w/w) EDTA disodium salt; 0.3% (w/w) sodium chloride salt; 0.05% (w/w) tyloxapol; 1.2% (w/w) sodium sulfate; and 0.25% (w/w) hydroxyethylcellulose; at pH range from 5.5 to 6.5.

It is known, of course, that EDTA can be in many forms such as a free acid, disodium, or tetrasodium salts. The steroid may be dexamethasone, prednisolone or prednisone. These steroids may be in their sodium phosphate form (e.g., dexamethasone sodium phosphate, prednisolone sodium phosphate, or prednisone sodium phosphate) or acetate form (e.g., dexamethasone acetate, prednisolone acetate, or prednisone acetate). Prednisolone is an active metabolite of prednisone and it is understood that prednisone may be used instead of prednisolone.

In a preferred embodiment, the ophthalmic composition retains at least 90% of its PVP-I and at least 90% of its steroid after 1 month, 2 months, 3 months, 6 months or 1 year after it is manufactured. This can be accomplished, at least, by producing the ophthalmic composition according to the formula listed above (e.g. previous two paragraphs). This stability is maintained even when the composition is stored at room temperature in a lighted indoor environment of 100 lux to 1000 lux. In one preferred embodiment, the composition is an aqueous solution.

In another embodiment, the invention is directed to a method for treating and/or prophylaxis of an eye disorder or a microorganism infection of at least one tissue of the eye comprising the step of administering one of more doses of an ophthalmic composition, discussed above, to the eye. The eye disorder may be, for example, a microorganism infection of at least one tissue of the eye, conjunctivitis, corneal abrasion, ulcerative infectious keratitis, epithelial keratitis, stromal keratitis and herpesvirus-related keratitis. The microorganism may be a bacteria (e.g., mycobacteria), virus, fungi, or amoebae.

In the method, the treatment may comprise administering a solution of the invention where the sum of the povidone-iodine, the anti-inflammatory, and the steroid is between 0.001 mg to 5 mg per dose. Further, the dose volume may be between 10 microliters to 200 microliters or between 50 microliters to 80 microliters; about one drop per eye. Administration may be between 1 to 24 times a day, between 2 to 4 times a day or between 2 to 24 times a day.

In one embodiment, the method further comprises a step of storing the solution for at least one month, at least two months, at least three months, at least six months, or at least one year before it is administered. The storage may be in a clear bottle (a container that does not substantially block light) in a lighted environment. A lighted environment may be, for example, an indoor lighted environment with about 100 lux to 1000 lux of light.

DETAILED DESCRIPTION OF THE INVENTION

In a preferred embodiment, the compositions of the present invention are administered topically. The dosage range is 0.001 to 5.0 mg/per eye; wherein the cited mass figures represent the sum of the three components: anti-inflammatory, povidone-iodine and topical anesthetic. Dosage for one eye is understood to be about one drop of solution. One drop of solution may be between 10 µl to 200 between 20 µl and 120 µl, or between about 50 µl (microliters) to about 80 µl of solution or any values in between. For example, dispensers such as pipettors can dispense fluid drops from at least 1 µl to 300 µl and any value in between.

In a preferred embodiment, the solution may be administered as an eye drop using any of the many types of eye drop dispensers on the market. Although not required, the container for the compositions of the invention may be clear, translucent, and opaque and may contain other properties or combination of properties such as being glass lined, tamper proof, packaged in single or few dose aliquots, and a combination thereof.

Povidone-iodine has the following chemical structure:

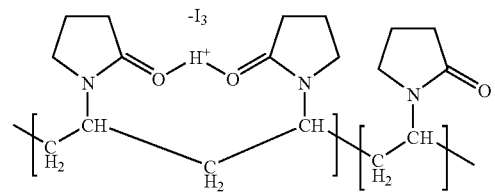

Suitable anti-inflammatories for the compositions and methods of the invention include, at least, the following: ketotifen fumarate, diclofenac sodium, flurbiprofen sodium, ketorlac tromethamine, suprofen, celecoxib, naproxen, rofecoxib, or a derivative or combination thereof. Ketorolac (also called ketorlac, or ketorolac tromethamine) a non-steroidal anti-inflammatory drug (NSAID) in the family of propionic acids.

Suitable steroids for the compositions and methods of the invention include, at least: dexamethasone, dexamethasone alcohol, dexamethasone sodium phosphate, fluoromethalone acetate, fluoromethalone alcohol, lotoprendol etabonate, medrysone, prednisolone, prednisone, prednisolone acetate, prednisolone sodium phosphate, rimexolone, hydrocortisone, hydrocortisone acetate, lodoxamide tromethamine, or a derivative or combination thereof. It is understood, for any of the chemicals of this disclosure, that the chemicals may be in various modified forms such as acetate forms, and sodium phosphate forms, sodium salts, and the like.

Dexamethasone has the following chemical structure:

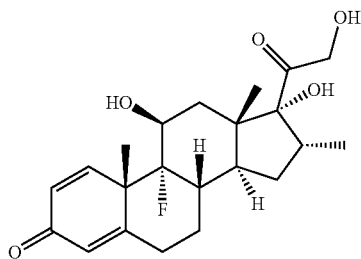

It is known that any of the reagents mentioned anywhere in this disclosure may be in chemically equivalent forms such as salts, hydrides, esters and other modifications of the basic chemical. For example, dexamethasone in any of the compositions and methods of the invention may be replaced with any of its derivatives, including esters and salts thereof. Examples of such derivatives include, at least, Dexamethasone-17-acetate (CAS RN: 1177-87-3), Dexamethasone Disodium Phosphate (CAS RN: 2392-39-4), Dexamethasone Valerate (CAS RN: 14899-36-6), Dexamethasone-21-isonicotinate (CAS RN: 2265-64-7), Dexamethasone Palmitate (CAS RN: 33755-46-3), Dexamethasone Propionate (CAS RN: 55541-30-5), Dexamethasone Acefurate (CAS RN: 83880-70-0), Dexamethasone-21-galactoside (CAS RN: 92901-23-0), dexamethasone 21-thiopivalate, dexamethasone 21-thiopentanoate, dexamethasone 21-thiol-2-methyl-butanoate, dexamethasone 21-thiol-3-methyl-butanoate, dexamethasone 21-thiohexanoate, dexamethasone 21-thiol-4-methyl-pentanoate, dexamethasone 21-thiol-3,3-dimethyl-butanoate, dexamethasone 21-thiol-2-ethyl-butanoate, dexamethasone 21-thiooctanoate, dexamethasone 21-thiol-2-ethyl-hexanoate, dexamethasone 21-thiononanoate, dexamethasone 21-thiodecanoate, dexamethasone 21-p-fluorothiobenzoate or a combination thereof. Dexamethasone derivatives are also described in U.S. Pat. No. 4,177,268.

Suitable topical anesthetics for the compositions and methods of the invention include, at least, proparacaine, lidocaine, tetracaine or a derivative or combination thereof.

The compositions of the present invention can be administered as solutions, suspensions, emulsions (dispersions), gels, creams, or ointments in a suitable ophthalmic vehicle.

In any of the compositions of this disclosure for topical administration, such as topical administration to the eye, the mixtures are preferably formulated as 0.01 to 2.0 percent by weight solutions in water at a pH of 5.0 to 8.0 (figures relate to combined presence of povidone-iodine and dexamethasone). This pH range may be achieved by the addition of buffers to the solution. We have found that, surprisingly, the formulation of the present invention is stable in buffered solutions. That is, there is no adverse interaction between the buffer and the iodine or other component that would cause the composition to be unstable. While the precise regimen is left to the discretion of the clinician, it is recommended that the resulting solution be topically applied by placing one drop in each eye 1 to 24 times daily. For example, the solution may be applied 1, 2, 4, 6, 8, 12, 18 or 24 times a day.

Antimicrobial Preservative

As an optional ingredient, suitable antimicrobial preservatives may be added to prevent multi-dose package contamination. Such agents may include benzalkonium chloride, thimerosal, chlorobutanol, methyl paraben, propyl paraben, phenylethyl alcohol, EDTA, sorbic acid, Onamer M, other agents known to those skilled in the art, or a combination thereof. Typically such preservatives are employed at a level of from 0.001% to 1.0% by weight.

Co-Solvents/Surfactants

The compositions of the invention may contain an optional co-solvent. The solubility of the components of the present compositions may be enhanced by a surfactant or other appropriate co-solvent in the composition. Such co-solvents/surfactants include polysorbate 20, 60, and 80, polyoxyethylene/polyoxypropylene surfactants (e.g. Pluronic F-68, F-84 and P-103), cyclodextrin, tyloxapol, other agents known to those skilled in the art, or a combination thereof. Typically such co-solvents are employed at a level of from 0.01% to 2% by weight.

Viscosity Agents

The compositions of the invention may contain an optional viscosity agent—that is, an agent that can increase viscosity. Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity builder agents include as examples polyvinyl alcohol, polyvinyl pyrrolidone, methyl cellulose, hydroxy propyl methylcellulose, hydroxyethyl cellulose, carboxymethyl cellulose, hydroxy propyl cellulose, other agents known to those skilled in the art, or a combination thereof. Such agents are typically employed at a level of from 0.01% to 2% by weight.

The Formulation

The following two reactions must be considered for the chemistry of PVP-I in aqueous solutions:

$$PVP\text{-}I_2 \rightleftharpoons PVP + I_2 \qquad\qquad a$$

$$PVP\text{-}HI_3 \rightleftharpoons PVP + H^{\oplus} + I_3^{\ominus} \qquad\qquad b$$

The affinity of free iodine ($I_2$) for reaction with —OH, —SH and —NH functional groups is well described in the literature and forms the basis for the anti-microbial activity of iodine-containing solutions (Rackur H. *J. Hosp. Infect.*, 1985; 6: 13-23, and references therein). Dexamethasone (9-Fluoro-11β, 17, 21-trihydroxy-16α-methylpregna-1,4-diene-3,20-dione) contains three such moieties (—OH) at the 11, 17 and 21 positions. A person in the field would conclude that these hydroxyl groups would be prone to covalent substitution reactions by the free iodine generated in the solution equilibrium reaction described above for $PVP\text{-}I_2$.

In deriving the present formulations, experiments of combinations of various anti-inflammatories and PVP-I, or steroids and PVP-I, were performed. It was observed that most formulations were unsuccessful because of the rapid reaction between PVP-I and the added reagent (anti-inflammatory or steroid). Some of these unsuccessful formulations are described elsewhere in this disclosure. Particularly, the limiting factor for lower concentrations of PVP-I solutions is stability and efficacy as a microbicidal.

It is thus the object of the present invention to discover novel formulation of combinations of PVP-I and an anti-inflammatory to solve three problems of stability, efficacy and non-irritating to the eye. We have found, unexpectedly, that a 1% PVP-I solution is effective for treatment of infection or prophylaxis of infections when combined with dexamethasone. The literature has previously indicated that while 1% PVP-I is desirable, the side effects of ocular administration precluded its use. The undesirable side effects include pain and irritation.

It was surprising to discover that the solution of PVP-I and dexamethasone remains stable for many months. Based on the stability data disclosed, we conjecture that the compositions of the invention may be stable for years—although experiments are still ongoing at this point. It is a further unexpected result that the reaction of dexamathasone and PVP-I does not proceed to any appreciable extent at room temperature, in light or dark, over time. Unexpectedly the reaction between the free iodine in solution and the hydroxyl groups present on the dexamethasone molecule as compounded in our formulation does not proceed.

Due to the high propensity of oxidative potential of PVP-I, the resulted stable combination of PVP-I and dexamethasone is unexpected for the average worker/scientist/physician in this field. It was observed when the concentration of PVP-I is larger than 0.5%, a stable combination formulation can be achieved. Surprisingly, it was found that 0.3% PVP-I combination with dexamethasone was much less stable. This is once again unexpected because the lower concentrations of iodine are expected to be less reactive and hence, less destructive to either parts. After 8 weeks, the available iodine in the combination (0.3% PVP-I initially) decreased by 20%. Though 0.1% diluted PVP-I has the strongest antimicrobial activity (Gottardi W. *J. Hosp. Infect.*, 1985; 6(Suppl): 1-11) our data showed we need at least 0.5% PVP-I in combination with dexamethasone to show the best antimicrobial activity. We have observed PVP-I reacted with Ketorolac (a non-steroidal anti-inflammatory) rapidly and the Ketorolac was completely consumed and the available iodine in the PVP-I complex was reduced significantly depending on the ratio between Ketorolac and PVP-I. The combination of PVP-I and dexamethasone sodium phosphate also proved to be less successful but also useful. We observed some dissociation of PVP-I complex to an unknown polymeric complex in the UV spectra and the iodine reduction is around 5% after 12 weeks. It was further observed that PVP-I reacts immediately with proparacaine and releases free iodine rapidly.

Surprisingly, the combination formulation has contributed to the stability of diluted PVP-I solution. The available iodine of a 0.625% povidone-iodine solution was 91% at 25° C. and 98% at 4° C. after 5 weeks storage, respectively. (*Iryo Yakugaku* 2003, 29(1), 62-65). Our data showed that our formulation stabilized the diluted PVP-I solution. After 8 weeks at room temperature, the available iodine in solutions with 0.5% and 1% PVP-I were over 99%.

The use of topical steroids alone is contraindicated in suspected viral and fungal infections of the human eye. Furthermore the use of combination anti-bacterial/steroid solutions is contraindicated in the setting of suspected viral infection. There are no steroid-containing solutions described that are safe for use in the human eye in the setting of presumed viral or fungal infection. It is therefore unexpected to the authors and others in the field that a steroid-containing solution would be of use in the treatment of an acute viral or fungal ocular infection.

A potent anti-inflammatory steroid allows the temperance of the potentially devastating ocular immune response in the setting of an active infection. However, due to the antiseptic (antibacterial, antiviral, and antifungal, antiprotozoal) power of PVP-I, the compound is useable in the setting of active infection without the risk of worsening the infection. This unique property (poly-antimicrobicide and potent anti-inflammatory) is a significant improvement over all other ocular antibiotics and anti-inflammatory.

Although a topical steroid is of tremendous benefit in the treatment of ocular inflammation, its use is fraught with risks. Topical steroids applied to the eye act by a variety of well described genomic and non-genomic mechanisms to reduce the production of constituent proteins of the inflammatory cascade, decrease vascular permeability, decrease the production of pro-inflammatory cytokines, decrease the potency of soluble inflammatory factors, inhibit the production of acute phase proteins, decrease leukocyte migration and increase the stability of cell membranes. Through all of these mechanisms, topically applied steroids can reduce the local concentrations of activated products toxic to the eye including the gelatinase, collaginase and matrixmetalloproteinase families of proteins. With this reduction in potentially toxic substances comes the increased risk of prolonged infection and potential infection. If the topical steroid is given in combination with an appropriate antimicrobial (i.e. and antibacterial for bacterial infection, an antiviral for viral infection, an antifungal for fungal infection) its risk can be reduced and/or eliminated. The usual practicing ophthalmologist cannot reliably distinguish the causative agent in most cases of acute external eye infection in a time frame relevant to the prescription of treatment. Thus the beneficial effects one may gain from the prompt use of topical steroids are delayed or eliminated entirely as the clinician either waits for culture results or more likely delays treatment indefinitely. The novel combination of a polymicrobicidal effective against bacteria, viruses and fungi and a topical steroid eliminates this risk and allows the immediate control of inflammation and eradication of pathogen. In our view, this is the most preferred embodiment of the present invention.

We also noted that the other components in our preferred composition appear to further stabilize the formulation. That is, the EDTA, sodium chloride, tyloxapol, sodium sulfate and hydroxyethylcellulose appear to have additional beneficial effects of further stabilizing the composition.

The invention has been described herein by reference to certain preferred embodiments. However, as obvious variations thereon will become apparent to those skilled in the art, the invention is not to be considered as limited thereto. All patents, patent applications, and references cited anywhere is hereby incorporated by reference in their entirety.

EXAMPLES

Throughout this section the letter "A" in a sample name refers to Povidone-Iodine complex ("PVP-I"), A00 refers to PVP-I at 0.0%, A03 refers to PVP-I at 0.3%, A05 refers to PVP-I at 0.5%, A10 refers to PVP-I at 1.0%, A15 refers to PVP-I at 1.5%, A20 refers to PVP-I at 2.0%, A40 refers to PVP-I at 4.0% and so on.

Similarly, the letter "B, C, D, K, P" in a sample name refers to dexamethasone, dexamethasone sodium phosphate, prednisolone sodium phosphate, ketorolac (also called ketorlac) and proparacaine, respectively. B00 refers to dexamethasone at 0.0%, B01 refers to dexamethasone at 0.1%, C01 refers to dexamethasone sodium phosphate at 0.1%, D01 refers to prednisolone sodium phosphate at 0.1%, K01 refers to ketorolac at 0.1%, and P008 refers to proparacaine at 0.08%, and so on.

Example 1

Production of Povidone-Iodine/Dexamethasone Suspensions

| | Amount (wt. %) |
|---|---|
| Povidone-Iodine (PVP-I) | 0.0 to 4.0 |
| Dexamethasone, Micronized, USP | 0.1 |
| EDTA, USP | 0.01 |
| Sodium Chloride, USP | 0.3 |
| Sodium Sulfate, USP | 1.2 |
| Tyloxapol, USP | 0.05 |
| Hydroxyethylcellulose | 0.25 |
| Sulfuric Acid and/or Sodium hydroxide | q.s. for pH adjustment to 5.7-6.0 |
| Sterile water, USP | q.s. to 100 |

Experimental Procedures:

In a 1000 mL beaker was added 400 g sterile water, hydroxyethylcellulose (2.25 g, 0.25% w/w) was added under vigorous stirring with an overhead stirrer. Sodium chloride (2.70 g, 0.3% w/w) was slowly added while dissolving, followed by addition of EDTA (0.09 g, 0.01% w/w) and sodium sulfate (10.8 g, 1.2% w/w). After stirring for 10 minutes, tyloxapol (0.45 g, 0.05% w/w) dissolved in water was transferred into the above solution. The reaction mixture was stirred for 1 hour and q.s. to 540 g with sterile water and was stirred for another 10 minutes to give "bulk solution 1."

60 g each of the bulk solution 1 was transferred into two 125 mL beakers, and povidone-iodine complex (0.5 g, 1.5 g) was added into the respective solution while stirring. The pH value was adjusted to the range of 5.7 to 6.0 by addition of sodium hydroxide or sulfuric acid and q.s. the suspensions to 100 g with sterile water to give control samples A05B00 and A15B00, respectively.

The remaining 417 g of the bulk solution 1 was added dexamethasone (0.7 g, 0.1% w/w) and homogenized for 5 minutes and then q.s. to 420 g to give bulk solution 2.

60 g each of the bulk solution 2 was transferred into seven 125 mL beakers, and povidone-iodine complex (0.0 g, 0.3 g, 0.5 g, 1.0 g, 1.5 g, 2.0 g, and 4.0 g) was added into the respective solution while stirring. The pH value was adjusted to the range from 5.7 to 6.0 by addition of sodium hydroxide or sulfuric acid and q.s. the suspensions to 100 g with sterile water to give samples A00B01, A03B01, A05B01, A10B01, A15B01, A20B01 and A40B01, respectively. The LC-MS spectra of all samples confirmed the finding that there was no reaction between PVP-I and dexamethasone at all. The dexamethasone ($MH^+$=392.9) peak has not been altered to other mass peaks.

Example 2

Production of Solutions of Povidone-Iodine/Dexamethasone Sodium Phosphate; Povidone-Iodine/Prednisolone Sodium Phosphate; and Povidone-Iodine/Ketorolac In a similar manner, solutions of A00C01, A03C01, A05C01, A10C01, A15C01, A00D01, A03D01, A05D01, A10D01, A15D01, A00K01, A05K01, A10K01, and A15K01 were produced.

The LC-MS spectra of A05C01, A10C01, and A15C01 confirmed the dexamethasone phosphoric acid ($MH^+$=472.9) peak. The LC-MS spectra of A05D01, A10D01, and A15D01 confirmed the prednisolone phosphoric acid ($MH^+$=440.9) peak.

However, the LC-MS experiments of A05K01 and A10K01 confirmed the finding of reaction between PVP-I and ketorolac tromethamine, For A05K01, there was a small amount of ketorolac left in the sample ($MH^+$=256.1), the major peak is: $MH^+$=381.9. For A10K01 and A15K01, there was no ketorolac left and has converted to a new compound ($MH^+$=381.9) completely.

LC-MS experiments of A00B01P008 (control), A05B01P008 and A10B01P008 confirmed the finding of reaction between PVP-I and proparacaine. For the control, two peaks: $MH^+$=295.1 (proparacaine) and $MH^+$=392.9 (dexamethasone) were observed in the LC-MS spectrum. Comparing A05B01P008 with A10B01P008, the proparacaine peak ($MH^+$=295.1) relative to the dexamethasone peak ($MH^+$=392.9) became much smaller, which suggests povidone iodine reacted with proparacaine.

Example 3

Production of Povidone-Iodine/Dexamethasone/Proparacaine Suspensions

| | Amount (wt. %) |
|---|---|
| PVP-I | 0.0 to 1.5 |
| Dexamethasone, Micronized, USP | 0.1 |
| Proparacaine hydrochloride, USP | 0.08% |
| EDTA, USP | 0.01 |
| Sodium Chloride, USP | 0.3 |
| Sodium Sulfate, USP | 1.2 |
| Tyloxapol, USP | 0.05 |
| Hydroxyethylcellulose | 0.25 |
| Sulfuric Acid and/or Sodium hydroxide | q.s. for pH adjustment to 5.7-5.9 |
| Sterile water, USP | q.s. to 100 |

In a 400 mL beaker was added 100 g sterile water, hydroxyethylcellulose (0.75 g, 0.25% w/w) was added under vigorous stirring with an ARROW overhead stirrer. Sodium chloride (0.9 g, 0.3% w/w) was slowly added while dissolving, followed by addition of EDTA (0.03 g, 0.01% w/w), sodium sulfate (3.6 g, 1.2% w/w) and proparacaine hydrochloride salt (0.24 g, 0.08% w/w) sequentially. After stirring for 10 minutes, tyloxapol (0.15 g, 0.05% w/w) dissolved in water was transferred into the above solution. The reaction mixture was stirred for 1 hour and dexamethasone (0.3 g, 0.1% w/w) was added and homogenized for 10 minutes and then q.s. to 180 g with sterile water to give the bulk solution 5. 60 g each of the bulk solution 5 was transferred into four 125 mL beakers, and povidone-iodine complex (0.0 g, 0.5 g, 1.0 g) was added into the respective solutions while stirring. The pH value was adjusted to around 5.8 by addition of sodium hydroxide or sulfuric acid and q.s. the solution to 100 g to afford samples A00B01P008, A05B01P008, and A10B01P008.

During the production of these samples, strong smell of iodine was observed. It was speculated that PVP-I reacted with proparacaine very rapidly. The speculation was confirmed by LC-MS spectra. The dexamethasone and proparacaine peaks in the combination samples with PVP-I became very small or even disappeared.

Stability of the Solutions

The amount of titratable iodine in the solutions was determined by titration method after various week of sample storage at room temperature.

Titration Method:

5 mL of each sample was transferred into a 125 mL beaker by pipette, and 1 mL of 1% (w/v) starch indicator solution was added. The solution was titrated with 0.0025N sodium thiosulfate solution until the blue color disappeared completely. The volume of sodium thiosulfate solution used was determined.

Titratable Iodine (mg)=$V$ (mL, volume used for titration)*12.69 (mg/mL)/2

The calculated titratable iodine (mg) is listed in Table 1.

TABLE 1

Stability Data Summary (Available Iodine)

| sample | Iodine (mg) 0 wk | Iodine (mg) After 1 wk | Iodine (mg) change % | Iodine (mg) after 8 wks | Iodine (mg) change % |
|---|---|---|---|---|---|
| CLSA05B00 | 2.32 | 2.25 | −3.02 | | |
| CLSA15B00 | 7.31 | 7.17 | −1.92 | | |
| CLSA03B01 | 1.36 | 1.27 | −6.62 | 1.08 | −20.59 |
| CLSA05B01 | 2.27 | 2.32 | 2.2 | 2.25 | −0.88 |
| CLSA10B01 | 4.28 | 4.28 | 0 | 4.25 | −0.7 |
| CLSA15B01 | 7.28 | 7.36 | 1.1 | 7.52 | 3.3 |
| CLSA20B01 | 9.87 | 9.9 | 0.3 | 9.71 | −1.62 |

| | Iodine (mg) (After 4 wks) | Iodine (mg) (After 12 wks) | Iodine (mg) change % |
|---|---|---|---|
| CLSA10C01 | 4.25 | 4 | −5.9 |
| CLSA15C01 | 6.79 | 6.54 | −3.7 |
| CLSA10D01 | 4.6 | 4.38 | −4.8 |
| CLSA15D01 | 6.44 | 6.41 | −0.5 |

| | 0 wk | After 5 wks | |
|---|---|---|---|
| CLSA05K01 | 1.81 | 0 | −100 |
| CLSA10K01 | 4.54 | 1.87 | −58.8 |
| CLSA15K01 | 7.17 | 4.57 | −36.3 |

The data of concentration of PVP-Iodine after weeks of storage at room temperature, either at dark or light, have suggested that stable combination formulations have been achieved for PVP-iodine combinations with dexamethasone, or dexamethasone sodium phosphate or prednisolone sodium phosphate. The 0.3% (wt. %) PVP-I combination with dexamethasone is less stable than those of above 0.5% PVP-Iodine combinations with dexamethasone, which have less than 5% alteration of the available iodine concentration after 8 weeks.

Data has also suggested PVP-I reacted with ketorolac tromethamine. At 0.5% PVP-I in the sample after five weeks, there was no titratable iodine left. At 1.5% and 1.5% of PVP-I in the samples, the titratable iodine was depleted significantly at 58.8% and 36.3%, respectively.

Stability Test of Dexamethasone in the Sample Using HPLC

The USP method was performed. The concentration of dexamethasone data is tabulated in chart form below in Table 2:

TABLE 2

| Samples | concentration (mg/mL)/3 wks | concentration (mg/mL)/7 wks | Concentration change % |
|---|---|---|---|
| CLS-A05B01 | 0.94 | 0.92 | −2.13 |
| CLS-A10B01 | 0.86 | 0.90 | 4.65 |
| CLS-A15B01 | 0.93 | 0.86 | −7.53 |

HPLC spectra have shown that there were no new peaks appearing compared with standard controls. The spectra suggested that there was no reaction between PVP-Iodine and dexamethasone at all.

Stability Test of Dexamethasone Sodium Phosphate in the Sample Using HPLC

The USP method was performed. The concentration data of dexamethasone sodium phosphate is tabulated in chart form below in Table 3. A05C01 (1 day), A10C01, A15C01 (3 days) in 40° C. oven.

TABLE 3

| Sample name | Initial Concentration (mg/mL) | Concentration (mg/mL) | Concentration Change % |
|---|---|---|---|
| A05C01 | 1.273 | 1.244 | −2.28 |
| A10C01 | 0.948 | 1.075 | 13.40 |
| A15C01 | 1.355 | 1.148 | −15.28 |

HPLC spectra have shown that there was a new peak appearing in the samples of A10C01 and A15C01 compared with standard controls and A05C01. The concentrations of dexamethasone sodium phosphate were altered more than 10% in the samples of A10C01 and A15C01.

In another experiment, we have found, surprisingly, that eye drops of the following formulation: 0.5 to 2% (w/w) polyvinylpyrrolidinone-iodine complex; 0.05 to 0.2% (w/w) steroid; 0.005% to 0.02% (w/w) EDTA; 0.01 to 0.5% (w/w) sodium chloride; 0.02 to 0.1% (w/w) tyloxapol; 0.5% to 2% (w/w) sodium sulfate; and 0.1 to 0.5% (w/w) hydroxyethylcellulose; wherein said steroid is dexamethasone, prednisolone, prednisone, or acetate forms thereof, or sodium phosphate forms thereof were stable for 1 month, 3 months and up to 6 months. Based on data gathered so far, such a solution appears to be capable of storage of up to at least 1 year from the date for manufacturer. Stability is defined as a deviation in concentration of the major components (PVP-I and steroid) by less than 10% over a period of time. Thus, the PVP-I was not reduced to less than 90% over the period of 1 month, 3 months, and 6 months while the solution is in storage and based on our data at 6 months, it appears that the solution would be stable for at least one year. Storage conditions was at room temperature, in clear bottles, in indoor lighting of 100 to 1000 lux of incandescent and/or fluorescent lighting. The stability may be attributed to the unique combination of PVP-I and dexamethasone, prednisolone, prednisone (including acetate forms and sodium phosphate forms of these steroids). We have additionally found that the other reagents (EDTA, sodium chloride, tyloxapol, sodium sulfate; and hydroxyethylcellulose) when present, further contributed to stability.

We have found, when comparing various formulations during development, that PVP-I confers a number of advantages in the formulation. Briefly, PVP-I formulations have the following improved properties compared to an iodine solution: (1) less irritating to the skin and eye, (2) washable, (3) increased stability, (4) increased stability in light, (5) low systemic toxicity, (6) less side effects. Also, based on current knowledge, PVP-I is neutral with respect to scar tissue formation.

Example 4

Antimicrobial Assays

Solutions of PVP-iodine combinations with various anti-inflammatory steroids were tested for antimicrobial activity against common pathogenic bacteria, yeast, fungi and viruses. The broth inoculation method of Antimicrobial Assays (USP) was used to conduct the efficacy test of the treatment of various concentrations of the solutions of PVP-iodine combinations against pure ocular isolates. It was found that the concentrations of PVP-iodine from 0.03% can dose-dependently produce the suppressing effects on microbial growth. The antimicrobial effects can be further supported by completely eliminating all species tested within 72 hours of inoculating treatment with 0.03% solution. The optimal efficacy of antimicrobial effects can be achieved at concentrations above 0.5%. Above the concentrations, the solution can effectively kill and eliminate all species tested even under a condition of immediate contact without further inoculation. For example, a solution of 1% PVP-iodine and 0.1% dexamethasone (wt %) was found to kill on contact *Pseudomonas aeuroginosa*, *Proteus mirabilis*, *Serratia maracescens*, *Staphylococcous aureus*, *Staphylococcus epidermidis*, *Streptococcus pneumoniae*, *Methicilin Resistant Staphylococcus Aureus*, *Klebsiella pneumoniae*, *Candida parapsilosis*, *Candida albicans* and *Apergillus niger*. The results clearly demonstrated the efficacy of the solutions on eliminating microbial growth.

Example 5

Adenovirus Testing

Solutions of PVP-iodine combinations with dexamethasone were tested for antiviral activity against human adenovirus. A 0.5 mL aliquot of each test and control article was combined with 0.5 mL of virus stock in a sterile tube. The tubes were then incubated at 37° C. for 30 minutes. A00B01 was used as the positive control. Hank's Balanced Salt Solution (HBSS) was used as the negative control. Immediately following incubation the test and control articles were titrated for infectious HAdV-4.

TABLE 4

| Antiviral Activity | |
|---|---|
| Customer Sample Number | HAdV-4 Titer (Log$_{10}$ TCID$_{50}$/mL) |
| A00B01 | 4.4 |
| A10B01 | ≤1.6 |
| A15B01 | ≤1.6 |
| A20B01 | ≤1.6 |
| HBSS | 4.0 |

Following a 30 minute incubation of the test articles with virus, A00B01 had no effect on virus infectivity, but compounds A10B01, A15B01 and A20B01 resulted in complete inactivation of the virus.

Example 6

Human Eye Irritation Studies

All volunteers were examined before testing and found to have healthy eyes with no signs of disease. 1.0% PVP-Iodine solution alone was made and tried in 15 healthy volunteers. Side effects of treatment were immediately reported. The side effects found included mild pain, discomfort, tearing, and redness. This is consistent because the literature has previously indicated that 1% PVP-iodine is unsuitable for use because of irritation that is unacceptable to the patient (e.g., U.S. Pat. No. 5,126,127). From the reported side effects, it is clear that a regiment of multiple applications to the volunteers would be intolerable.

The solution of A10B01, containing 1% PVP-1 and 0.1% dexamethasone, was tested by seven healthy volunteers. Administration was by eye drop. It was surprisingly found that the solution was tolerable to the eye (does not burn) and was comfortable at a range of pH. Specifically, the formulation of pH 5.9 formulation is comfortable upon instillation into the eye. One person used the solution as an eye drop four times a day for a period of 3 days with no adverse side effects. Other pH values, such as pH 6 to 8, are obtainable either by adjusting the pH alone, with a suitable chemical such as sulfuric acid or sodium hydroxide, or by the addition of a suitable buffer.

All volunteers were examined by physicians immediately after the trial period and in further follow-up examinations after a period of time. Further, volunteers were contacted by physicians at one month, two months and three months after trial and no adverse effects were reported for any of the volunteers.

We claim:
1. A composition comprising a mixture of
  a) povidone-iodine in a concentration of about 10% by weight, and
  b) a steroid, wherein the steroid is dexamethasone, and wherein, after a period of one month after mixing the steroid and povidone-iodine to form the composition, the steroid concentration is at least 90% of the steroid starting concentration.
2. A composition comprising a mixture of
  a) povidone-iodine, wherein the povidone-iodine is at a concentration selected from the group consisting of about 2.0% by weight and about 4% by weight by weight; and
  b) a steroid, wherein the steroid is dexamethasone, and wherein, after a period of one month after mixing the steroid and povidone-iodine to form the composition, the steroid concentration is at least 90% of the steroid starting concentration.

* * * * *